(12) United States Patent
Burling et al.

(10) Patent No.: US 7,763,236 B2
(45) Date of Patent: Jul. 27, 2010

(54) USE OF OSTEOPONTIN IN DENTAL FORMULATIONS

(75) Inventors: Hans Burling, Lund (SE); Esben Skipper Sørensen, Sabro (DK); Hans Bertelsen, Videbæk (DK); Anders Steen Jørgensen, Århus C (DK); Gitte Graverholt, Århus N (DK)

(73) Assignee: Arla Foods Amba, Viby (DK)

( * ) Notice: Subject to any disclaimer, the term of this patent is extended or adjusted under 35 U.S.C. 154(b) by 0 days.

(21) Appl. No.: 12/363,661

(22) Filed: Jan. 30, 2009

(65) Prior Publication Data

US 2009/0202449 A1    Aug. 13, 2009

Related U.S. Application Data

(63) Continuation of application No. 11/000,028, filed on Dec. 1, 2004, now abandoned.

(60) Provisional application No. 60/525,828, filed on Dec. 1, 2003.

(30) Foreign Application Priority Data

Dec. 1, 2003    (DK) .............................. 2003 01777

(51) Int. Cl.
*A61K 8/21* (2006.01)
*A61K 9/68* (2006.01)

(52) U.S. Cl. ........................... 424/49; 424/51; 424/52; 424/435; 424/440

(58) Field of Classification Search .................... 514/2, 514/12; 424/49, 85.1, 51–52, 435, 440
See application file for complete search history.

(56) References Cited

U.S. PATENT DOCUMENTS 6,875,422 B2 *    4/2005   Nonomura et al. ............ 424/49

FOREIGN PATENT DOCUMENTS

WO           WO 0228413 A1 *    4/2002

* cited by examiner

*Primary Examiner*—Nashaat T Nashed
*Assistant Examiner*—Marsha M Tsay
(74) *Attorney, Agent, or Firm*—Finnegan, Henderson, Farabow, Garrett & Dunner, L.L.P.

(57) ABSTRACT

Use of osteopontin for reducing plaque bacterial growth on tooth enamel and dental formulations containing osteopontin.

16 Claims, 1 Drawing Sheet

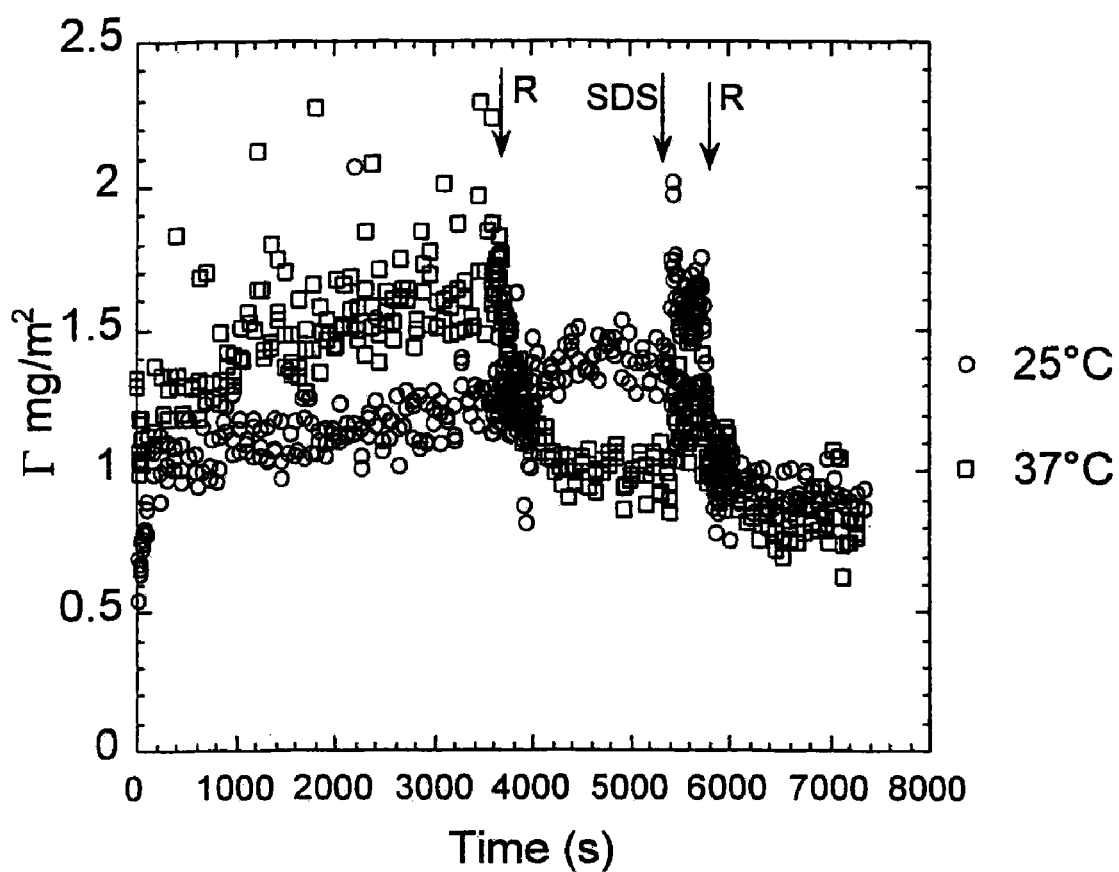

USE OF OSTEOPONTIN IN DENTAL FORMULATIONS

This is a continuation of application Ser. No. 11/000,028, filed Dec. 1, 2004, now abandoned which claims priority to Danish Patent Application No. PA 2003 01777, filed Dec. 1, 2003, and claims the benefit of U.S. provisional application No. 60/525,828, filed Dec. 1, 2003, all of which are incorporated herein by reference.

TECHNICAL FIELD OF THE INVENTION

The present invention concerns dental formulations. In particular the invention concerns the use of osteopontin (OPN) for significantly reducing plaque bacterial growth on tooth enamel.

BACKGROUND OF THE INVENTION

Many problems occur in connection with care of the teeth, cosmetically as well as therapeutically, such as formation of dental plaque, bacterial growth in dental plaque, dental caries, dental calculus (tartar), periodontal disease and demineralization of teeth. Dental plaque is a complex biofilm that accumulates on the hard tissues (teeth) in the oral cavity. Although over 500 bacterial species comprise plaque, colonization follows a regimented pattern with adhesion of initial colonizers to the enamel salivary pellicle followed by secondary colonization through bacterial adhesion. It is well known that a range of streptococci species belong to the early colonizers. It is therefore important to control the adhesion of these bacteria. A variety of adhesins and molecular interactions underlie the adhesive interactions and contribute to plaque development and ultimately to diseases such as caries and periodontal disease.

The enamel of teeth is comprised of hydroxyapatite. In the mouth a natural equilibrium exists between, on the one hand, hydroxyapatite being dissolved from the enamel of the teeth and, on the other, hydroxyapatite being formed on or in the teeth from substances occurring naturally in the saliva. When the equilibrium is such that the hydroxyapatite is dissolved, a cariogenic condition arises which is referred to as demineralization.

It has long been known that incorporation of fluoride ions into enamel protects it from demineralization. Therefore, fluoride is often incorporated in toothpaste. However, fluoride can give rise to fluorose, especially if the patient is swallowing the toothpaste or another dentrifice or oral hygiene product, which is often the case, for example for small children. It can also be a problem in areas with rather high amounts of fluoride in the drinking water.

The purpose of this patent application is to propose the use of an indigenous milk protein, osteopontin, added to a dental formulation to control or inhibit the growth of bacteria on the tooth surface and thereby prevent or reduce plaque formation and caries.

There are a couple of patents that describe the use of milk protein fractions, i.e. hydrolysates of casein, Ca phosphopeptides/CPP, and glucomacro-peptide/GMP from renneting of milk for repair of damage to the enamel with the hypothesis that they act as a supply of amorphous calcium phosphate to the enamel.

WO 03/059304 proposes an oral care composition containing a fluoride ion source and CPP fraction. This formulation stabilizes the calcium phosphate added to the oral formulation in an amorphous form and at the same time stabilizes the fluoride level in the formulation.

WO 00/07454 describes GMP which, added to a special food formulation based on milk, has an anticariogenic effect on rats.

In contrast to CPP and GMP peptides, OPN introduces a new dimension in the oral cavity, through its potential to bioactively influence the attachment of oral organisms to the enamel and thus affect the development of caries. Like CPP and GMP, OPN also has an effect on the levels of amorphous calcium phosphate in the saliva available for tooth repair.

OPN thus has several functions in the dental care context.

The great advantage of using OPN in e.g. toothpaste and mouthwash is that it is a natural protein component in bovine milk and thus there is a limited need for clinical testing.

SUMMARY OF THE INVENTION

It has now surprisingly been shown that osteopontin used in oral formulations reduce bacterial adherence and growth on enamel surfaces.

The invention is about oral compositions, containing osteopontin including toothpaste, mouthwash and chewing gum as well as related compositions.

BRIEF DESCRIPTION OF THE DRAWING

The FIGURE is a graphical representation of the adsorption of OPN on a hydroxyapatite disc measured by ellipsometry at different temperatures. R symbolizes rinsing of the surface with buffer and SDS symbolizes rising with sodium dodecyl sulphate.

DETAILED DESCRIPTION OF THE INVENTION

An in vitro study using a tooth analogue of a finely polished hydroxyapatite (HA) disc dipped in a dilute solution of OPN gives a film of OPN on the HA surface, which cannot be washed away with water. When such treated discs were brought into contact with human saliva surprisingly we found that the film of OPN significantly reduced the adherence and growth of bacteria on the analogue tooth surfaces resulting in a significantly lower plaque formation. The trials were made using saliva samples from a group of patients of different ages and oral flora. These results implicate the potential use of OPN in oral formulations such as toothpaste and mouthwash but also as an ingredient in chewing gum.

Therefore the invention relates to the use of osteopontin for reducing plaque bacterial growth on tooth enamel and dental formulations containing osteopontin.

As used herein the term "osteopontin" or "OPN" means osteopontin obtained from milk, including naturally occurring fragments or peptides derived from OPN by proteolytic cleavage in the milk, or genesplice-, phosphorylation-, or glycosylation variants as obtainable from the method proposed in WO 01/49741. The milk can be milk from any milk producing animals, such as cows, camels, goats, sheep, dromedaries and llamas. However, OPN from bovine milk is preferred due to the availability. All amounts are based on native bovine milk OPN, but can easy be corrected to the corresponding amounts of an active fraction thereof or OPN from another source. OPN or derivates thereof can also be genetically prepared.

The dental formulations can be any dentifrice or related product of relevance in oral hygiene, such as for example toothpowder, tooth gel, dental mouthwash, mouth spray or chewing gum. Osteopontin (OPN) is an acidic, highly phosphorylated, sialic acid rich, calcium binding protein. OPN binds 28 moles of phosphate and about 50 moles of Ca per mole. The isoelectric point is about 3.0. The protein exists in many tissues in the body and plays a role as a signaling and regulating protein. It is an active protein in biomineralization processes. OPN is expressed by a number of cell types including bone cells, smooth muscle cells and epithelial cells.

OPN is present in bovine milk. A typical concentration is 20 mg per 1. OPN can relatively simply be isolated by anion chromatography from e.g. acid whey at pH 4.5 as described by patent WO 01/497741 A2 or WO 02/28413. Purity of up to 90-95% can easily be obtained.

The amount of osteopontin is normally between about 50 mg OPN and about 1500 mg osteopontin per kg dental formulation. However, smaller amount will also have an effect. Higher amounts can be used, but the effect will not be essentially increased. A useful amount is 100-1000 mg OPN per kg, preferably 200-500 mg, and most preferred about 350 mg. Larger amounts will presumably not give better results and is therefore not recommended, because OPN is a rather expensive ingredient.

Preferred compositions of the subject invention are as already mentioned in the form of as tooth-pastes, tooth-gels and tooth powders. Components of such toothpaste and tooth-gels include one or more of the following: a dental abrasive (from about 10% to about 50%), a surfactant (from about 0.5% to about 10%), a thickening agent (from about 0.04% to about 0.5%), a humectant (from about 0.1% to about 3%), a flavoring agent (from about 0.04% to about 2%), a sweetening agent (from 0.1% to about 3%), a coloring (from about 0.01% to about 0.5%) and water (from 2% to 45%). Anticaries agents contain from 0.001% to about 1% OPN. Anti-calculus agents contain from about 0.1% to about 13% OPN.

Tooth powders, of course, are substantially free from all liquid components. Other preferred compositions of the subject invention are dental mouth washes, including mouth sprays. Components of such mouth washes and mouth sprays typically include one or more of the following: water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent from (from about 0.1% to about 3%). and a coloring agent (from about 0.001% to about 0.5% anti-caries agent including OPN, from about 0.001% to 1% and an anti-calculus agent (from about 0.1% to about 13%).

A third area of application is in chewing gum formulations of various compositions in general terms.

The invention is further illustrated by the following examples and experiments.

Examples

Background

It was the purpose of this study to prove two things:

OPN binds to hydroxyapatite surfaces in a stable way. The film cannot be removed by rinsing with water or buffer.

OPN influences the adherence of bacteria on the tooth analogue surface.

The ability of OPN to prevent plaque build-up in-vitro has been investigated in this study on hydroxyapatite (HA) discs acting as a model for tooth enamel. The discs were dipped in OPN solution and subsequent incubated with saliva. Growth on the substrates was studied with bacterial count of different plaque-forming bacterial strains at the Faculty of Odontology at Malmö University, Sweden.

As a reference for OPN coated HA surfaces, non-coated and BSA (bovine serum albumin) treated HA discs were used.

The study was performed on well characterized saliva samples from 6 donors as described below.

Materials and Methods

Chemicals

Osteopontin (OPN) was prepared by Aria Foods amba with a chromatographic purity of about 95%. Bovine serum albumin (BSA) was purchased from Sigma-Aldrich. Sodium dodecylsulphate (SDS) was obtained from Sigma (St. Louis, Mo., USA, L-6026). All other chemicals were of analytical grade and the water used was of Milli-Q quality. Pre-treatments of substrates and adsorption experiments were performed in phosphate buffer containing 0.01 M phosphate and 0.05 M sodium chloride at pH 7. All glassware and pipette tips, etc as well as buffers were sterilized by autoclavation. Protein solutions used in experiments were sterilized by filtration (cut-off 0.22 μm).

Salivary Samples

Stimulated saliva for the experiments was collected after chewing a piece of paraffin. A summary of the donors of stimulated salivary samples is shown in Appendix 1.

No food or drink was allowed two hours prior to collection.

Substrates

Hydroxyapatite (HA) discs, 10 mm in diameter, were purchased from Swedish Ceramic Institute, Göteborg. The discs used for SEM studies were polished on both sides so that they could be cleaned using ultrasound. Before starting the experiments, substrates (discs) were treated in mild detergent solution and thoroughly rinsed in water. Finally, they were rinsed in ethanol and water. Substrates were stored in 70% ethanol until use when they were rinsed with water and dried in a flow of nitrogen. After drying, substrates used in ellipsometry measurements were plasma cleaned in low pressure residual air (10-30 Pa) using a radio frequency glow discharge unit (Harrick PDC 3XG, Harrick Scientific Corp., Ossining, N.Y.).

Bacterial Film Formation

Substrate surfaces were pre-incubated for 1 h in protein solution at 37° C. Substrates were then rinsed with buffer and incubated at 37° C. for 40 h. Stirring was applied during pre-treatment and incubation in the experiments. After incubation the HA discs were rinsed with buffer.

Ellipsometry

The interaction of OPN with salivary proteins on HA substrates was followed by ellipsometry, which is an optical method to measure the changes in polarization of light upon reflection at a surface (3). The instrument used was a Rudolph thin film ellipsometer, type 436 (Rudolph Research, Fairfield, N.J.), equipped with a xenon lamp filtered to 4015 A, and operated in a set-up as described by Landgren and Jönsson (1993).

To determine the ellipsometric angles, $\Delta$ and $\Psi$, for the bare substrate the position of the intensity minimum was established. From the changes in $\Delta$ and $\Psi$ upon adsorption the thickness and the refractive index for the adsorbed protein film were calculated according to McCrackin et al. (4) assuming a homogeneous film at the surface. The adsorbed mass, $\Gamma$ ($mg/m^2$), was calculated according to Cuypers et al. (5). As shown by these authors, the adsorbed mass can, at low surface coverage, be determined more accurately than the film thickness and the refractive index, and has for this reason been presented here. The values of the ratio between molar weight and molar refractivity and of the partial specific volume used were 4.1 g/ml and 0.75 ml/g, respectively. These values are commonly used for proteins and have previously been applied in a number of studies regarding adsorption of salivary components (cf. (6, 7)). Surfaces prepared as described in the substrate section above were placed in the ellipsometer cuvette containing the buffer. The cuvette was thermostated at 37° C. unless otherwise stated, and the solution was stirred with a magnetic stirrer. When the ellipsometric angles were stable saliva was added to a final concentration of 10% (v/v). The adsorption was measured for 1 h followed by rinsing of the cuvette with a continuous buffer flow of 12 ml/min for 5 min. The desorption was then followed for another 25 min. This was the standard procedure for pellicle formation. In order to obtain a measure of the cohesive properties of the pellicle the experiments featured a final addition of SDS. In the standard experiment a concentration of 17 mM (twice the cmc in water and approximately nine times the cmc in buffer) was added and after this a final rinse with buffer was performed 5 min after the SDS addition.

Methods for Microbiological Analyses

Culture Medium

The basic agar media employed for the isolation of micro organisms were blood agar (8), Mitis Salivarius agar (MSA, Difco Lab.), Mitis Salivariusbacitracin (MSB) agar (9), Candida Selective agar according to Nickerson (Merck), Mac Conkey agar (Difco Lab) and *Staphylococcus* medium 110 (Difco Lab).

Culturing Procedures for Saliva Samples

Saliva samples were transported in conventional VMG II (viability preserving) medium, vortex-mixed within 24 h of collection, diluted and inoculated onto blood, MSA and MSB agars. Blood agar was incubated in an anaerobic chamber (10% hydrogen, 10% carbon dioxide in nitrogen) for 4 days and, MSA agar in an atmosphere of 5% carbon dioxide for 2 days. The total number of colony-forming units (CFU) on the agar plates was counted with the aid of a stereomicroscope.

Removal of Micro Organisms from the Discs

The micro organisms attached to the discs were removed by sonication in a Sonics Vibracell with a microtip using 10 pulses of 1 second. Removal of cells by sonication was confirmed to be efficient by the lack of observed microbial growth.

Culturing Procedures for Desorbate Samples

The desorbate samples were vortex-mixed, diluted and inoculated into the following media: blood agar, MSA, Candida Selective agar, Mac Conkey agar and *Staphylococcus* medium 110. Blood agar was incubated in an anaerobic chamber (10% Hydrogen, 10% Carbon Dioxide in Nitrogen) for 5 days, the MSA in an atmosphere of 5% Carbon Dioxide for 2 days and, Candida Selective agar, Mac Conkey agar and *Staphylococcus* medium 110 aerobically for 2 days. The total number of CFU on the agars was counted with the aid of a stereomicroscope. The CFU on MSA was analyzed paying special attention to morphology, size and number of different colony types. Cells from representative colonies of each morphological type were Gram-stained and inoculated on blood agar for later identification. For future characterization, isolates growing on the MSA were retained at −79 C in skim milk (10% skim milk powder in distilled water, w/v; Oxoid Lab. L31, Hampshire, UK).

Identification of Streptococcal Isolates Gram-positive, catalase negative cocci in chains were considered to be streptococci and these isolates will be identified to species and subspecies levels based on characteristics described previously (10).

Results and Discussion

Protein Interaction Study

In order to investigate the interaction between OPN and HA and OPN and saliva an ellipsometry study was performed. In FIG. 1 the effect of adsorption temperature is shown. From this FIGURE it can be seen that the adsorption of OPN on the HA surfaces happens almost instantaneously. A larger amount of OPN was absorbed at higher temperature (37° C.), although, rinsing resulted in some desorption at 37° C. to a stable surface load of 1 mg per $m^2$. To simulate the chemical effect of tooth brushing SDS was added to the cuvette for five minutes, followed by rinsing with buffer. After this cleaning step there was no significant difference in adsorbed amount at the two temperatures.

The results obtained indicate that OPN gives a surface coverage of the HA discs that is stable although a reduction in film thickness is obtained after water rinse and SDS treatment.

Bacterial Film Formation

The counts of bacteria shown in table 1 and 2 desorbed by mild sonication show for HA discs treated with OPN solutions with concentration 0.1 mg/ml and 1 mg/ml respectively a significant effect on adherence of bacteria both in total counts on blood agar and MSA agar plates for all salivary donors. HA discs treated with BSA or saliva exhibited more bacteria on the surfaces. The total counts of micro organisms were 10- to 1000-fold lower on OPN-coated discs than on the control discs (saliva or BSA-coated). The stimulated saliva samples exhibited a highly diverse microbial composition which is considered to be a common characteristic of the salivary microflora. Of interest was the finding that significantly fewer streptococci colonized the OPN-coated than the control discs.

TABLE 1

Bacterial analysis of whole discs, polished on both sides incubated in stimulated saliva after different pre-treatments.

| | Pre-treatment | | | |
| Donor | BSA | Saliva | OPN 0.1 | OPN 1 |
| --- | --- | --- | --- | --- |
| ME | 33.000 | 6.800 | 102 | 0 |
| K | 12.600 | 5.200 | 280 | 48 |
| Br | 45.200 | 71.400 | 8.800 | 4.800 |
| ML | 19.900 | 41.000 | 7.100 | 13.800 |
| Be | | 6.700 | 1.280 | 3.400 |

Total count (CFU) on blood agar plates incubated anaerobically.

TABLE 2

Bacterial analysis of whole discs, polished on both sides incubated in stimulated saliva after different pre-treatments.

| | Pre-treatment | | | |
| Donor | BSA | Saliva | OPN 0.1 | OPN 1 |
| --- | --- | --- | --- | --- |
| ME | 19 | 50 | 15 | 0 |
| K | 9.400 | 44 | 11 | 1 |
| Br | 1.220 | 2.140 | 480 | 960 |
| ML | 2.190 | 360 | 30 | 90 |
| Be | 120 | 120 | 30 | 70 |

Total count on Mitis Salivarious Agar (MSA) incubated facultatively anaerobically.

SUMMARY

The results show a clear effect of OPN pre-treatment of HA discs on the amount of bacteria after incubation in stimulated saliva. The anti-adhesive effect seems to be almost concentration independent in the range investigated 0.1-1 mg/ml of OPN solution for dipping of the tooth analogues. For a monolayer coverage a small amount of OPN is needed.

It is interesting to note that significantly less streptococci adherence the OPN-coated discs compared with the control discs.

REFERENCES

1. Hanh Berg, C, et al.
2. Dawes, C., "Rhythms in Salivary flow Rate and Composition", International Journal of Chronobiology, 2 (1974) 253-279.
3. Azzam, R. M. A. and Bashara, N. M., Ellipsometry and Polarized Light, North-Holland Amsterdam, 1977.
4. McCrackin, F. L., Passaglia, E., Stromberg, R. R. and Steinberg, H. L., "Measurement of the Thickness and Refractive Index of very Thin Films and Optical Properties of Surfaces by Ellipsometry", J. Res. Nat. Bur. Stand., A67 (1963) 363-377.
5. Cuypers, P. A., Corsel, J. W., Janssen, M. P., Kop, J. M. M., Hermens, W. T. and Hemker, H. C., "The adsorption of Prothrombin to Phosphatidylserine Multilayers Quantitated by Ellipsometry", J. Biol. Chem., 258 (1983) 2426-2434.
6. Vassilakos, N., Arnebrant, T. and Glantz, P.-O., "Adsorption of Whole Saliva onto Hydrophilic and Hydrophobic Solid Surfaces. The Influence of Concentration, Ionic Strength and pH.", Scand. J. Dent. Res., 100 (1992) 346-353.
7. Vassilakos, N., Arnebrant, T., Rundegren, J. and Glantz, P.-O., "In vitro Interactions of Anionic and Cationic Surfactants with Salivary Fractions on Well Defined Solid Surfaces.", Acta Odontol. Scand, 50 (1992) 179-188.
8. Beighton D, Russell R R B, Whiley R A; A simple biochemical scheme for the differentiation of *Streptococcus mutans* and *Streptococcus sobrinus*: Caries Res 1991; 25:174-178.
9. Gold O G, Jordan H V, van Houte J: A selective medium for *Streptococcus mutans*. Arch Oral Biol 1973; 18:1357-1364.
10. Holdeman L V, Cato E P, Moore W E C: Anaerobe Laboratory Manual, ed 4. Blackbury, Anaerobic Laboratory, Virginia Polytechnic Institute and State University, 1977.

The invention claimed is:

1. A method for inhibiting plaque bacterial growth on tooth enamel by administering, a formulation in the form of a toothpaste, mouthwash, mouth spray or chewing gum, comprising an amount of osteopontin effective to inhibit plaque bacterial growth.

2. The method according to claim 1, wherein the amount of osteopontin is about 5 mg to about 1500 mg osteopontin per kg of formulation.

3. The method according to claim 1, wherein the amount of osteopontin is about 100 mg to about 1000 mg osteopontin per kg of formulation.

4. The method according to claim 1, wherein the amount of osteopontin is about 200 mg to about 500 mg osteopontin per kg of formulation.

5. The method according to claim 1, wherein the amount of osteopontin is about 350 mg to about 500 mg osteopontin per kg of formulation.

6. The method according to claim 1, wherein osteopontin is the only anti-bacterial agent in the formulation.

7. A method according to claim 2, wherein the formulation further comprises at least one of (by weight):
   about 10% to about 50% dental abrasive;
   about 0.5% to about 10% surfactant;
   about 0.04% to about 0.5% thickening agent;
   about 0.1% to about 3% humectant; and
   from 2% to 45% water.

8. A method according to claim 2, wherein the formulation further comprises at least one of (by weight):
   about 45% to about 95% water;
   about 0% to about 25% ethanol; and
   about 0.01% to about 7% surfactant.

9. A method of treating the teeth of a patient in need of inhibiting plaque bacterial growth on tooth enamel by administering to the teeth a formulation comprising an amount of osteopontin effective to inhibit plaque bacterial growth.

10. The method according to claim 9, wherein the amount of osteopontin is about 5 mg to about 1500 mg osteopontin per kg of formulation.

11. The method according to claim 9, wherein the amount of osteopontin is about 100 mg to about 1000 mg osteopontin per kg of formulation.

12. The method according to claim 9, wherein the amount of osteopontin is about 200 mg to about 500 mg osteopontin per kg of formulation.

13. The method according to claim 9, wherein the amount of osteopontin is about 350 mg to about 500 mg osteopontin per kg of formulation.

14. The method according to claim 9, wherein osteopontin is the only anti-bacterial agent in the formulation.

15. A method according to claim 10, wherein the formulation further comprises at least one of (by weight):
   about 10% to about 50% dental abrasive;
   about 0.5% to about 10% surfactant;
   about 0.04% to about 0.5% thickening agent;
   about 0.1% to about 3% humectant; and
   from 2% to 45% water.

16. A method according to claim 10, wherein the formulation further comprises at least one of (by weight):
   about 45% to about 95% water;
   about 0% to about 25% ethanol; and
   about 0.01% to about 7% surfactant.

* * * * *